United States Patent [19]

Giner-Sorolla

[11] 4,221,910
[45] Sep. 9, 1980

[54] 9-(HYDROXY ALKYL)PURINES

[75] Inventor: Alfredo Giner-Sorolla, Riverside, Conn.

[73] Assignees: Newport Pharmaceuticals Intern, Inc., Calif.; Sloan-Kettering Instit. for Cancer Res., New York, N.Y.

[21] Appl. No.: 942,804

[22] Filed: Sep. 15, 1978

[51] Int. Cl.³ .......................................... C07D 473/30
[52] U.S. Cl. ..................................... 544/265; 424/253
[58] Field of Search ......................... 544/265, 264, 271

[56] References Cited

U.S. PATENT DOCUMENTS

| | | | |
|---|---|---|---|
| 3,314,938 | 4/1967 | Kawashima et al. | 544/264 |
| 3,632,742 | 1/1972 | Eckers et al. | 544/271 |
| 3,813,394 | 5/1974 | Tensho et al. | 544/265 |
| 3,862,189 | 1/1975 | Schwender | 544/265 |
| 4,031,218 | 6/1977 | El-Antably | 544/273 |

OTHER PUBLICATIONS

Schaeffer et al., Biochemistry, vol. 4 71–76 (1965).
Schaeffer et al., J. Med. Chem 17 6 (1974).
Schaeffer et al., J. Med. Chem 15 456 (1972).

Primary Examiner—Nicholas S. Rizzo
Attorney, Agent, or Firm—Cushman, Darby & Cushman

[57] ABSTRACT

There are prepared compounds of the formula

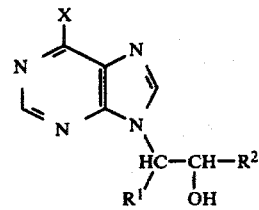

where X is OH, $R^2$ is $CH_3$ and $R^1$ is alkyl of 1 to 8 carbon atoms. The compounds are immunopotentiators, have antiviral activity and anti-leukemic activity.

6 Claims, No Drawings

9-(HYDROXY ALKYL)PURINES

The invention described herein was made in the course of work under a grant or award from the Department of Health, Education and Welfare.

SUMMARY OF THE INVENTION

The present invention is directed to compounds of the formula

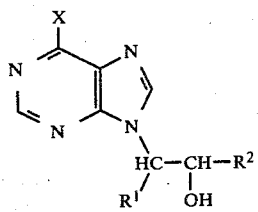

where X is OH, $R^2$ is $CH_3$ and $R^1$ is alkyl of 1 to 8 carbon atoms. The compounds are immunopotentiators, have antiviral activity and anti-leukemic activity. They can also be reacted with amine salts of p-acetamidobenzoic acid to form complexes which in some cases enhance the activities mentioned above. The complexes have the formula

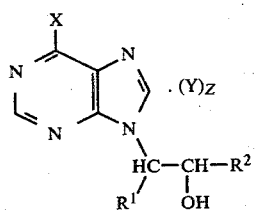

Y is the salt of an amine of the formula

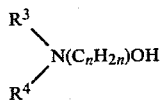

where $R^3$ and $R^4$ are lower alkyl, e.g., of 1 to 4 carbon atoms, e.g., methyl, ethyl, propyl, butyl, isopropyl or isobutyl, n is an integer of 2 to 4 with p-acetamidobenzoic acid and where z is a number from 1 to 10.

Immunoregulatory activity appears to increase with increasing chain length for $R^1$, at least from methyl through hexyl. Preferably $R^1$ is n-alkyl, i.e., methyl, ethyl, n-propyl, n-butyl, n-amyl, n-hexyl, n-heptyl or n-octyl. Typical examples of amines for forming the acetamidobenzoic acid salts include dimethylamino ethanol, dimethylamino isopropanol, diethylamino ethanol, diethylamino isobutanol, diethylamino isopropanol, methyl ethyl amino ethanol, diisobutylamino-N-butanol, dimethylamino propanol, dimethylamino-N-butanol, diisobutylamino ethanol, dimethylamino butanol, dibutylamino-N-butanol, dibutylamino ethanol, dipropylamino ethanol and diisopropylamino ethanol. The presently preferred amine is dimethylamino isopropanol. When Y is present, i.e., z is 1 to 10, preferably z is 3. However, z can also be 1, 2, 4, 5, 6, 7, 8, 9 or 10.

Also rather than the compounds where Y is the salt of the amine

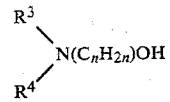

with p-acetamidobenzoic acid there can also be prepared salts of the formula $Y^1$ wherein the amine is as just defined and the acid is a pharmaceutically acceptable acid other than p-acetamidobenzoic acid, e.g., hydrochloric acid, sulfuric acid, hydrobromic acid, phosphoric acid, acetic acid, propionic acid, malonic acid, lactic acid, citric acid, tartaric acid, p-toluene sulfonic acid, adipic acid, maleic acid, succinic acid, methane sulfonic acid, salicyclic acid, acetyl salicyclic acid.

In describing the compounds below, when Y is present the abbreviation DIP.PAcBA stands for dimethylamino-2-propanol-p-acetamido benzoate. Unless a number in parentheses, e.g. (10), follows this abbreviation, then Y is 3. If a number in parentheses follows the abbreviation DIP.PAcBA there the number indicates the number of moles of Y groups present to 1 mole of the 9-(hydroxyalkyl)purine.

In Table 1 below the compounds are believed to be pure except for compound 15443 which is believed to also contain a salt in addition to the compound of the invention.

An immunomodulator is a compound which regulates the immune response. Thus it covers both immunostimulation (immunopotentiation) and immunoinhibition. Immunostimulation, of course, is useful in building up immunity. Immunoinhibition also has utility in a number of areas. For example, it is useful in organ transplants, e.g., kidney or heart transplants, to prevent organ rejection.

In the tables showing the immunopotentiating properties of the compounds, a plus (+) indicates immunopotentiating properties, a minus (−) indicates immunoinhibiting properties. The number 0 indicates the compound had neither immunopotentiating activity nor immunoinhibiting activity.

There are included in some of the tables a number of compounds wherein variations of X and $R^2$ are not within the claimed compounds. The uses of these non-claimed compounds as well as of the claimed compounds as immunoregulators, antiviral agents and antitumor agents is presented in the application of Lionel H. Simon and John W. Hadden, filed on even date entitled "Immunomodulators and Antiviral Agents".

A mitogen is a substance which induces cell proliferation. As occurs during immunization.

Table 1 shows the compounds of the invention as well as related compounds differing in the definitions of X, $R^1$ and $R^2$.

The synthetic procedures A through L mentioned in Table 1 are described in more detail subsequently.

The compositions of the invention are useful in treating mammals (and cells of mammals) including humans, swine, dogs, cats, cattle, horses, sheep, goats, mice, rabbits, rats, guinea pigs, hamsters, monkeys, etc.

Unless otherwise indicated, all parts and percentages are by weight.

All temperatures are in degrees centigrade unless otherwise indicated.

The compositions can comprise, consist essentially of or consist of the materials set forth and the processes can comprise, consist essentially of or consist of the steps set forth with such materials.

The compositions can be administered to the mammals by conventional techniques, e.g., orally, nasally, rectally, vaginally, or parenterally. They can be employed as injectable solutions, e.g., in water, or as tablets, pills, capsules, etc.

TABLE 1a-continued

| $R^1$ | $R^2$ | COMPOUND X | Y |
|---|---|---|---|
| $C_2H_5$ | $CH_3$ | OH | — |
| $C_2H_5$ | $CH_3$ | OH | DIP . PAcBA |
| $C_3H_7$ | $CH_3$ | OH | — |
| $C_3H_7$ | $CH_3$ | OH | DIP . PAcBA |

TABLE 1
SUMMARY OF CHEMICAL PROPERTIES OF 9-(HYDROXYALKYL) PURINES

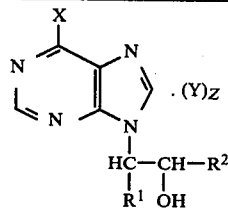

| No. | $R^1$ | $R^2$ | X | Y | Synthetic Method | M.Pt. °C. | λMax. | λMin. | Con $10^{-3}$ | pH | C | H | N |
|---|---|---|---|---|---|---|---|---|---|---|---|---|---|
| 15425 | H | H | OH | — | D | 274° | 250 | 222.5 | 11.93 | 7 | | | |
| | | | | | | | 250 | 219 | 11.0 | 1 | | | |
| | | | | | | | 254 | 221.5 | 12.53 | 10 | | | |
| 15428 | H | H | OH | DIP . PAcBA | L | | | | | | | | |
| 15435 | H | H | SH | — | C | 278°–80° | 323 | 251 | 23.0 | 7 | | | |
| | | | | | | | 323 | 252 | 19.9 | 1 | | | |
| | | | | | | | 323 | 251 | 19.9 | 10 | | | |
| 15437 | H | H | SH | DIP . PAcBA | L | | | | | | | | |
| 15446 | H | $CH_3$ | OH | — | A | 224°–5° | 250 | 223.5 | 11.0 | 7 | | | |
| | | | | | | | 250 | 220 | 10.6 | 1 | | | |
| | | | | | | | 254 | 223.5 | 12.1 | 10 | | | |
| 15447 | H | $CH_3$ | OH | DIP . PAcBA | L | | | | | | | | |
| 15431 | H | $CH_3$ | $NH_2$ | — | B | 188° | 261 | 228 | 15.8 | 7 | Cal 49.73 | 5.74 | 36.25 |
| | | | | | | | 259 | 231 | 15.4 | 1 | FD 49.56 | 5.62 | 36.22 |
| | | | | | | | 261 | 225 | 15.7 | 10 | | | |
| 15432 | H | $CH_3$ | $NH_2$ | DIP . PAcBA | L | | | | | | | | |
| 15427 | $CH_3$ | H | I | — | E | 178° | 276 | 237 | 10.9 | 7 | Cal 31.60 | 2.98 | 18.43 |
| | | | | | | | 276 | 237 | 10.9 | 1 | FD 31.53 | 2.96 | 18.18 |
| | | | | | | | 276 | 237 | 10.9 | 10 | | | |
| 15423 | $CH_3$ | H | Cl | — | F | 200°–204° | 265 | 228 | 9.1 | 7 | Cal 45.20 | 4.26 | 26.36 |
| | | | | | | | 265 | 228 | 9.1 | 1 | FD 45.11 | 4.27 | 26.25 |
| | | | | | | | 265 | 228 | 9.1 | 10 | | | |
| 15433 | $CH_3$ | H | $NH_2$ | — | G | 215°–16° | 261.5 | 228 | 13.56 | 7 | | | |
| | | | | | | | 259 | 231 | 13.26 | 1 | | | |
| | | | | | | | 261 | 224.5 | 13.80 | 10 | | | |
| 15434 | $CH_3$ | H | $NH_2$ | DIP . PAcBA | L | | | | | | | | |
| 15443 | $CH_3$ | H | OH | — | H | 198°–199° | 250 | 223 | 7.52 | 7 | | | |
| | | | | | | | 250 | 218 | 6.91 | 1 | | | |
| | | | | | | | 255 | 225.5 | 7.91 | 10 | | | |
| 15444 | $CH_3$ | H | OH | DIP . PAcBA | L | | | | | | | | |
| 15417 | $C_6H_{13}$ | H | OH | — | I | 226° C. | 250 | 224 | 11.09 | 7 | Cal 59.07 | 7.65 | 21.16 |
| | | | | | | | 250 | 220 | 10.37 | 1 | FD 59.01 | 7.55 | 21.24 |
| | | | | | | | 255 | 223 | 11.96 | 10 | | | |
| 15418 | $C_6H_{13}$ | H | OH | DIP . PAcBA | L | | | | | | | | |
| 15392 | $C_6H_{13}$ | $CH_3$ | OH | — | J | 202° C. | 250 | 224 | 12.1 | 7 | Cal 60.41 | 7.97 | 20.13 |
| | | | | | | | 248 | 222 | 13.3 | 1 | FD 60.47 | 7.86 | 20.08 |
| | | | | | | | 254 | 220 | 14.1 | 10 | | | |
| 15410 | $C_6H_{13}$ | $CH_3$ | OH | DIP . PAcBA | L | | | | | | | | |
| 15426 | $C_6H_{13}$ | $CH_3$ | $NH_2$ | HCl Salt | K | 176°–9° C. | 261 | 230 | 9.77 | 7 | Cal 53.58 | 7.71 | 22.32 |
| | | | | | | | 259 | 233 | 9.60 | 1 | FD 53.56 | 7.67 | 22.34 |
| | | | | | | | 261 | 235 | 9.77 | 10 | | | |

Other compounds within the invention and related p-acetamidobenzoic acid salts are set forth in Table 1a below wherein the basic formula is the same as that in Table 1. In Tables 1 and 1a, the alkyl groups for $R^1$ are all n-alkyl.

TABLE 1a

| $R^1$ | $R^2$ | COMPOUND X | Y |
|---|---|---|---|
| $C_6H_{13}$ | $CH_3$ | OH | DIP . PAcBA(10) |
| $C_6H_{13}$ | $CH_3$ | OH | DIP . PAcBA(1) |
| $CH_3$ | $CH_3$ | OH | — |
| $CH_3$ | $CH_3$ | OH | DIP . PAcBA |
| $C_4H_9$ | $CH_3$ | OH | — |
| $C_4H_9$ | $CH_3$ | OH | DIP . PAcBA |
| $C_5H_{11}$ | $CH_3$ | OH | DIP . PAcBA |
| $C_5H_{11}$ | $CH_3$ | OH | — |
| $C_7H_{15}$ | $CH_3$ | OH | — |
| $C_7H_{15}$ | $CH_3$ | OH | DIP . PAcBA |
| $C_8H_{17}$ | $CH_3$ | OH | — |
| $C_8H_{17}$ | $CH_3$ | OH | DIP . PAcBA |

DESCRIPTION OF THE PREFERRED EMBODIMENTS AND METHODS OF MAKING AND USING COMPOUNDS OF THE INVENTION AND RELATED COMPOUNDS

Method A
9-(2-HYDROXY-1-PROPYL)HYPOXANTHINE (NPT 15446)

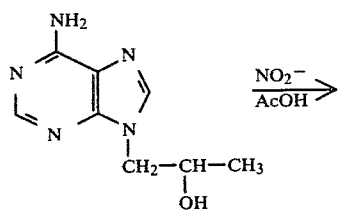

9-(2-Hydroxy-1-propyl)adenine (I, 4.0 g, 20.7 mmol) was suspened in 50% acetic acid (20 ml) and sodium nitrite (4 g, 58 mmol), was slowly added. The mixture was stirred at 25° for 3 hr. The resulting solution was evaporated to dryness and isopropanol added; this operation was repeated once. The solid residue was boiled in isopropanol and filtered. The filtrate was evaporated and crystallized by addition of acetone. Recrystallization was made from iso-propanol/methanol (98:2); a colorless crystalline product was obtained. Yield 3.3 g (82%); M.P. 244°–250°; uv ($H_2O$; pH 5.5), $\lambda$max 250 nm.

Method B
9-(2-HYDROXY-1-PROPYL)-6-CHLOROPURINE

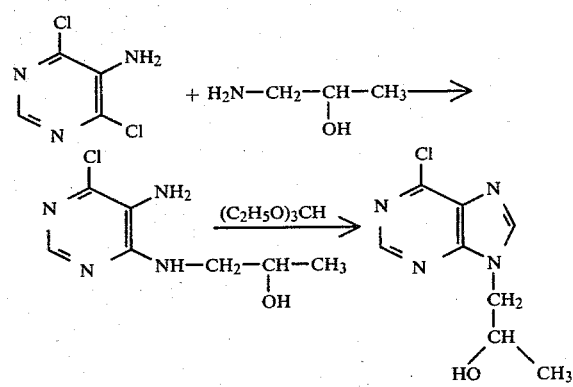

There were employed the methods of Schaeffer, H. J., Vogel, D. and Vince, R., J. Med. Chem. 8,502 (1965); and Schaeffer, H. J. and Vince, R., J. Med. Chem. 10, 689 (1967).

A solution of 5-amino-4,6-dichloropyrimidine (I, 20 g, 0.12 mole) in 11% ethanolic solution of isopropanolamine (200 ml) was refluxed for 8 hr. The reaction mixture was evaporated to a syrup, ethanol added and evaporated again; this operation was repeated once. The resulting syrup was poured into water (300 ml) giving a crystalline mass. It was collected by filtration, washed with water and dried to give 19 g of crude 9-(2-hydroxy-1-propylamino)5-amino-6-chloropyrimidine (II).

The crude compound II was suspended in triethylorthoformate (120 ml) to which ethanesulfonic acid (5 drops) was added. After 15 min. all the solid dissolved and the solution was kept at 25° overnight. Evaporation in vacuo gave a thick syrup which was submitted to high vacuo evaporation to remove the excess of isopropanolamine. Upon crystallization with xylene, 5 g of crude material was obtained.

Method B
9-(2-HYDROXY-1-PROPYL)ADENINE (NPT 15431)

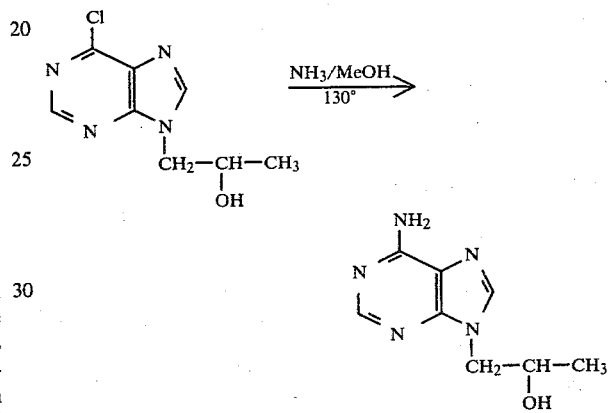

9-(2-Hydroxy-1-propyl)-6-chloropurine (I, 9 g, 42.5 mmol) was dissolved in saturated methanolic ammonia and ammonium chloride (50 mg). The mixture was heated at 130° in a bomb for 6 hr. The resulting solution was evaporated to dryness and recrystallized from ethanol/acetone. Yield=6.68 g of a colorless crystalline product (81%); mp 193°–194°; uv ($H_2O$; pH 5.5), $\lambda$max 260 nm; TLC in $CHCl_3$:MeOH (5:1); $R_f$ 0.44.

Anal. Calc. for $C_8H_{11}N_5O$: C, 49.73; H, 5.74; N, 36.25; Found: C, 49.56, H, 5.62; N, 36.22.

Method C
9-(1-HYDROXYETHYL)-6-MERCAPTOPURINE (NPT 15435)

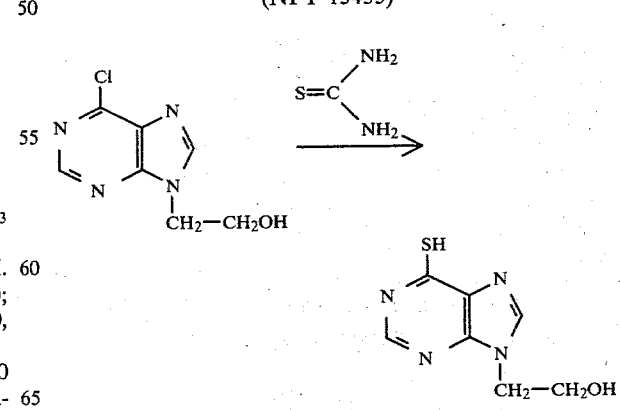

There was employed the method of Schaeffer and Bhargava, Biochemistry 4, 71 (1965).

9-(1-Hydroxyethyl)-6-chloropurine (I, 2 g, 0.01 mol) and thiourea (0.76 g; 0.01 mol) were dissolved in ethanol (15 ml) and refluxed for 30 min. The resulting precipitate was collected by filtration and suspended in water to form a slurry. Neutralization with sodium acetate gave colorless crystals. Yield 1.5 g (76%).

M.P. 278°–280°; uv (H$_2$O, pH 5.5) λmax 320, 230 nm.

Method D

9-HYDROXYETHYL HYPOXANTHINE (NPT 15425)

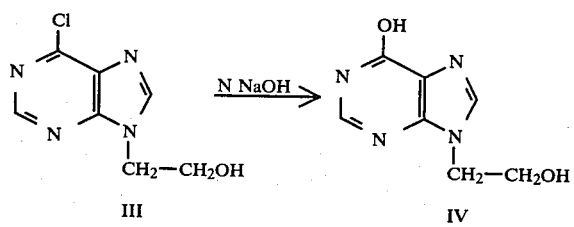

There was used the method of Schaeffer, H. J. and Bhargava, P. S., Biochemistry 4, 71 (1965).

6-Chloro-9-hydroxyethyl purine, III (4 g), was added slowly to warm N NaOH (30 ml) and refluxed for 2 hr. The reaction is cooled in ice and neutralized with glacial acetic acid. After filtration, portions of unreacted III are removed. The product is recrystallized from methanol and washed with acetone. Colorless crystals. Yield, 1 g. (28%) mp. 274°; uv (H$_2$O, pH 5.5), λmax 250 nm.

Method E

9-(1-HYDROXYL-2-PROPYL)-6-IODOPURINE (NPT 15427)

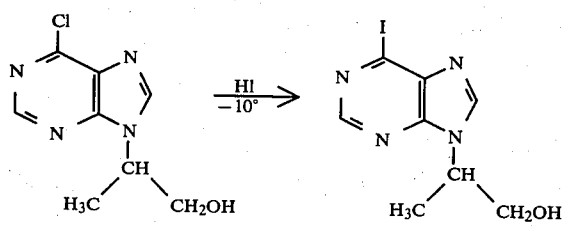

9-(1-Hydroxy-2-propyl)-6-chloropurine (I, 1.5 g, 7 mmol) was added to hydroiodic acid (15 ml) at −10° with stirring for 45 min. The precipitate was filtered, neutralized with anhydrous sodium acetate at 5°, and washed with a little cold water (3 times). Recrystallization from ethanol/H$_2$O, gave colorless crystals. Yield=0.9 g (42%); mp=193°–194°; uv λmax 276 nm (H$_2$O, pH 5.5).

Anal. Calc. for C$_8$H$_9$N$_4$OI MW=304.1: C, 31.60; H, 2.98; N, 18.43; I, 41.73. Found: C, 31,53; H, 2.96; N, 18.18; I, 41.70.

Method F

9-(1-HYDROXY-2-PROPANE)-6-CHLOROPURINE (NPT 15423)

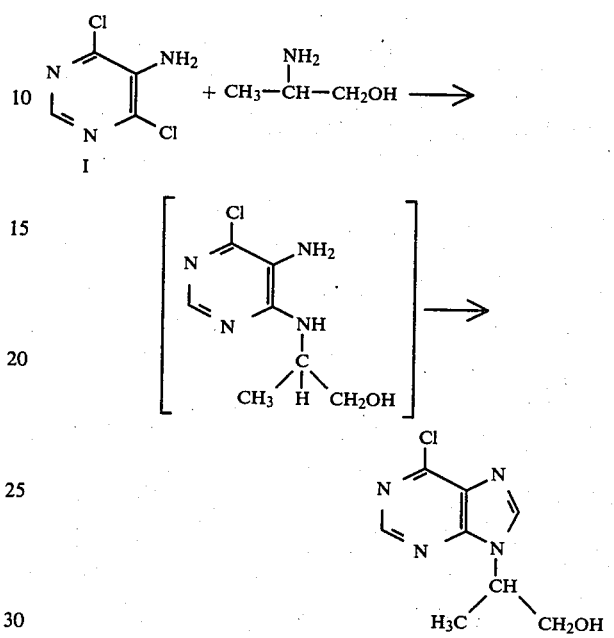

There was used the method of Schaeffer, H. J. and Schwender, C. F., J. Med. Chem. 17, 6 (1974).

A solution of 5-amino-4,6-dichloropyrimidine (I, 6.56 g 40 mmol) and 2-amino-1-propanol (II, 3.3 g, 44 mmol) was refluxed in n-pentanol (288 ml) and tert-butylamine (96 ml) for 45 hr. under N$_2$ atmosphere. The solution was evaporated to a syrup and ethanol added 4 times and evaporated. The resulting syrup was suspended in triethylorthoformate (150 ml) and ethanesulfonic acid (10 drops). The suspension was vigorously stirred overnight, then evaporated to dryness, ethanol added and this operation repeated three times. Crystallization of colorless product occurs during evaporation. The crystals were filtered, and the filtrate was evaporated, ethanol added and this operation repeated three times to give a crude material (3.6 g).

Recrystallized from 98% aqueous ethanol. uv (H$_2$O, pH 5.5) λmax 265 nm; mp 201°–203°; yield 2.79 (32%):

Anal. C$_8$H$_9$N$_4$OCl. Calc. C, 45.20; H, 4.26; N, 26.36; Cl, 16.68. Found: C, 45.11; H, 4.27; N, 26.25; Cl, 16.71.

Method G

9-(1-HYDROXY-2-PROPYL)ADENINE (NPT 15433)

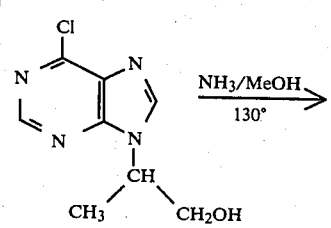

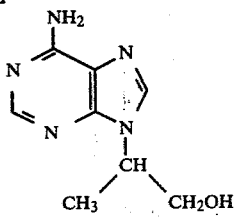

There was used the procedure of Schaeffer, H. and Schwender, C., J. Pharm. Sci., 60, 1204 (1971). Also Schaeffer et al., J. Med. Chem. 15, 456 (1972).

9-(1-Hydroxy-2-propyl)-6-chloropurine (I, 2.0 g, 9.4 mmol) was suspended in methanol/ammonia (30 ml) and ammonium chloride (50 mg) added as a catalyst and the mixture heated at 130° for 4.5 hr; the solution was evaporated to dryness. Recrystallization from ethanol of the obtained crude product gave colorless needles. Yield=1.15 g (63%) mp=215°–216° uv (H$_2$O, pH 5.5) λmax, 260 nm.

Method H

9-(1-HYDROXY-2-PROPYL)HYPOXANTHINE (NPT 15443)

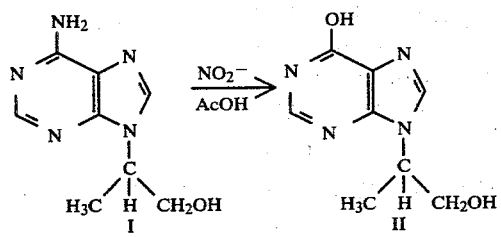

9-(1-Hydroxy-2-propyl)adenine (I, 4 g, 21 mmol) was dissolved in 50% acetic acid (20 ml), sodium nitrite (4 g, 58 mmol) added and the mixture stirred at 25° for 3½ hr. The solution was evaporated to dryness twice with isopropanol. The residue was taken up in isopropanol and filtered, the precipitate discarded, and the filtrate evaporated to form a gel which, upon the addition of acetone, solidified. Yield=3.65 (90%) of colorless crystals. Recrystallized from isopropanol/methanol (98:2). mp=202°–207°; TLC in CHCl$_3$:MeOH (5:1); 1 spot R$_f$ 0.30; uv (H$_2$O, pH 5.5)=λmax 250 nm.

Method I

COMPOUND NPT 15417

There was used the procedure of Schaeffer et al, Journal of Pharmaceutical Sciences 16:1204–1210, Method F.

The product is compound XL in Table III of Schaeffer et al.

Method J

ERYTHRO-9-(2-HYDROXY-3-NONYL)HYPOXANTHINE (NPT 15392)

An outline of the synthetic sequence for the preparation of erythro-9-(2-hydroxy-3-nonyl)hypoxanthine (Nonylhypoxanthine, VIII) is shown in Flow Charts 1 and 2. The improvements over the procedure of H. J. Schaeffer and C. F. Schwender, J. Med. Chem., 17, 6 (1974) in the reaction sequence leading to the erythro-9-(2-hydroxy-3-nonyl)-6-chloropurine (VII) are indicated. The last step, the hydrolysis of the 6-chloropurine derivative (VII), to yield nonylhypoxanthine (VIII) is an adaptation of the method reported by A. Giner-Sorolla, C. Gryte, A. Bendich and G. B. Brown, J. Org. Chem. 34, 2157 (1969) for the hydrolysis of halogenopurines.

The alternate route, i.e., the nitrosation of erythro-9-(2-hydroxy-3-nonyl)adenine (EHNA) (IX), to yield Nonylhypoxanthine (VIII) (shown on Flow Chart 2) consists of the previous conversion by ammonolysis of the chloro derivative (VII) into the aminopurine (IX, EHNA) followed by its nitrosation to yield Nonylhypoxanthine (VIII).

Flow Chart 1

OUTLINE OF THE SYNTHESIS OF ERYTHRO-9-(2-HYDROXY-3-NONYL)HYPOXANTHINE (VIII)

Step 1

ACETAMIDONONAN-2-ONE (II)

Acylation of 2-amino octanoic acid

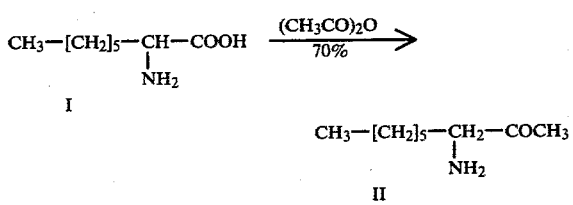

Step 2

ACETAMIDONONAN-2-ONE HYDROCHLORIDE (III)

Formation of the acetamidononan-2-one hydrochloride

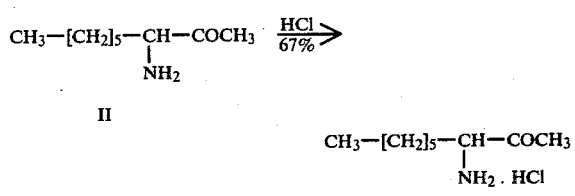

Step 3

ERYTHRO-3-AMINO-2-NONANOL (IV)

Reduction of the acetamidononan-2-one hydrochloride

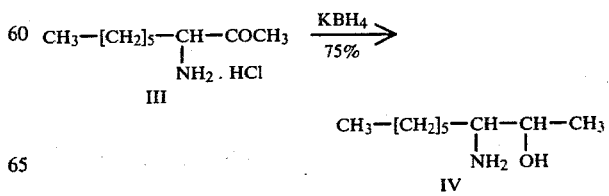

(Figures below the arrow refer to % yield.)

Step 4

ERYTHRO-5-AMINO-4-CHLORO-6-(2-HYDROXY-3-NONYLAMINO)PYRIMIDINE (VI)

Condensation of erythro-3-amino-2-nonanol with 5-amino-4,6-dichloropyrimidine

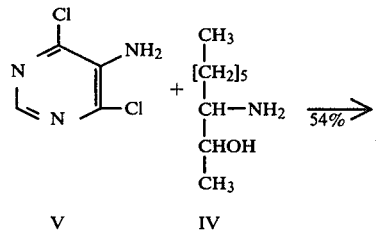

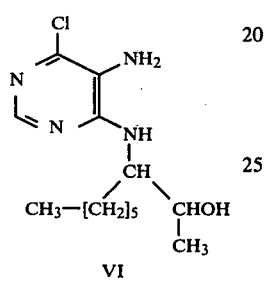

Step 5

ERYTHRO-9-(2-HYDROXY-3-NONYL)-6-CHLOROPURINE (VII)

Ring closure of erythro-5-amino-4-chloro-6-(2-hydroxy-3-nonylamino)pyrimidine (V)

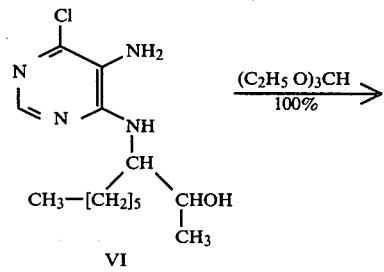

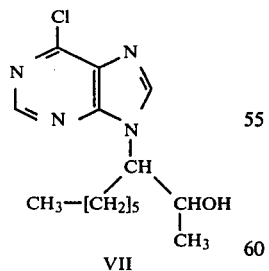

Step 6

ERYTHRO-9-(2-HYDROXY-3-NONYL)HYPOXANTHINE (VIII)

(By hydrolysis of the 6-chloropurine derivative)

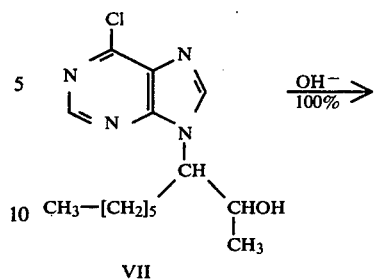

Flow Chart 2

ALTERNATIVE ROUTE FOR THE PREPARATION OF ERYTHRO-9-(2-HYDROXY-3-NONYL HYPOXANTHINE (VIII)

Step 1a

ERYTHRO-9-(2-HYDROXY-3-NONYL)ADENINE (IX)

Ammonolysis of erythro-9-(2-hydroxy-3-nonyl)-6-chloropurine (VII)

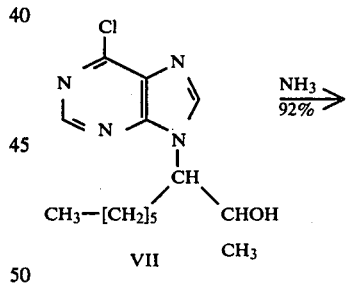

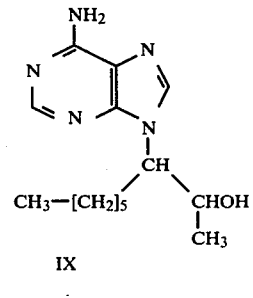

Step 2b

ERYTHRO-9-(2-HYDROXY-3-NONYL)HYPOXANTHINE (VIII)

Nitrosation of erythro-9-(2-hydroxy-3-nonyl)adenine (IX)

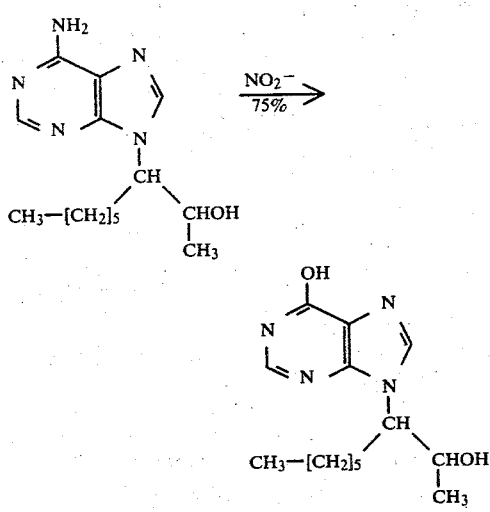

3-ACETAMIDONONAN-2-ONE (II)

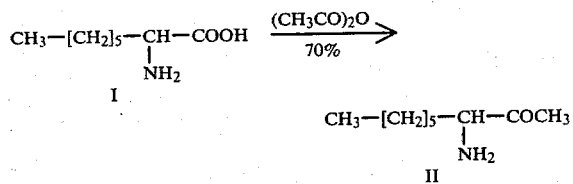

A mixture of 2-amino-1-octanoic acid (I, 200 g, 1.26 mole) in acetic anhydride (960 ml), and pyridine (640 ml) was heated on a boiling water bath for 4 hr. The reaction mixture was evaporated in vacuo, and the residue was partitioned 6-8 times between 5% aqueous solution of NaHCO₃ (400 ml) and ether (400 ml). The combined ethereal extracts were dried with anhydrous MgSO₄ and evaporated to dryness to give crude 3-acetamidononan-2-one, 154 g (70%).

3-AMINO-2-NONANONE HYDROCHLORIDE (III)

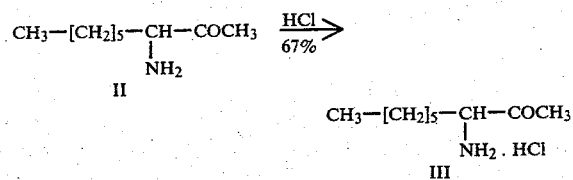

The crude product (II) obtained in the preceding operation (154 g) was dissolved in concentrated aqueous HCl (1,540 ml) and refluxed for 2 hr. and then evaporated to dryness in vacuo. The resulting solid was recrystallized from a warm solution in EtOH (200 ml) and then cooled to 25°. To this solution ether (600 ml) was added. A white crystalline precipitate appears; the suspension is kept at 5° overnight. The precipitate is collected and washed with ether (once with 100 ml) to give 125 g (67%) white crystalline product M.P. 112° dec.

If the crystalline material were not white or had a lower melting point, it should be recrystallized with charcoal from tetrahydrofuran. In one repeat of this procedure there was used 150 ml of hydrofuran for 100 g of the crude hydrochloride (III).

ERYTHRO-3-AMINO-2-NONANOL (IV)

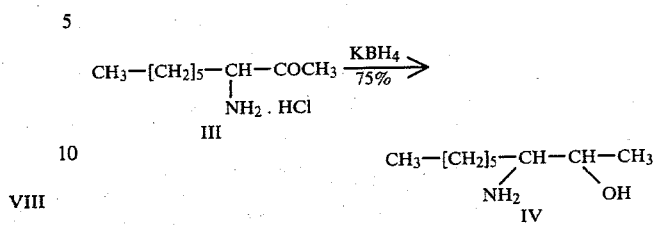

3-Amino-2-nonanol hydrochloride (43.8 g, 0.226 mole) was dissolved in absoulte methanol (150 ml) and cooled to −10° in an ice-salt bath. 1/ Potassium borohydride (24.4 g, 0.45 mole) 2/ was added in small portions over a 2-3 period. The mixture is then kept at −10° to −15° for 3 hr. 3,4/ and slowly allowed to reach room temperature (22°), then stirred overnight (20 hr.) at room temperature. The mixture is then evaporated to dryness (syrup) in vacuo and partitioned between H₂O (150 ml) and chloroform (150 ml). The H₂O layer was further extracted (3x) with chloroform (100 ml ea.). The chloroform layer was dried with MgSO₄ and evaporated in vacuo to give a slightly yellowish, oily product. This liquid was distilled in high vacuo at 95°-100° (0.15 mm Hg) to give pure erythro-3-amino-2-nonanol, 26.4 g, 75% yield, m.p. 81°-86°.

1. Upon cooling the solution of III, some material precipitates; this has no effect on the outcome of the reaction.
2. At this point, the present procedure differs from that of Schaeffer et al. Schaeffer adds acetic acid at the same time as KBH₄, maintaining the pH at 5-6. It has been found that neutralization entails loss of KBH₄ and that a pH above 5 is tolerated. More important is the fact that the simultaneous addition of acetic acid and KBH₄ (as proposed by Schaeffer) makes the reaction very difficult to control. The temperature raises considerably and losses in yield and/or quality of the product occur.
3. It is recommended to use an efficient stirring to insure the proper reaction which will be completed when all the small lumps and portions of potassium borohydride have disappeared.
4. Cooling at 0°, as described by Schaeffer et al (Method, D, line 4 and ff.) is insufficient. It is an improvement to keep the reaction well below 0°; it is best to keep it below −10° all the time. If the temperature is allowed to go over −10°, substantial loss in yield may result.

ERYTHRO-5-AMINO-4-CHLORO-6-(2-HYDROXY-3-NONYLAMINO)PYRIMIDINE (VI)

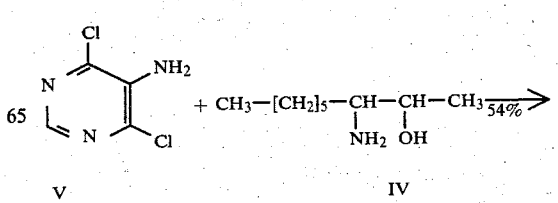

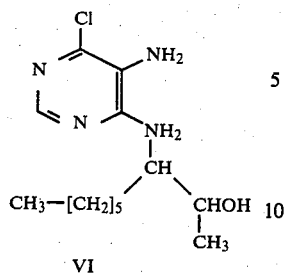

A mixture of 4,6-dichloro-5-aminopyrimidine (V, 24.6, 0.15 mole) and erythro-3-amino-2-nonanol (IV, 26.2 g, 0.164 mole) in 1-pentanol (1.080 ml) and tributylamine (350 ml) was prepared with stirring at 25°. The resulting suspension was heated to reflux under nitrogen atmosphere for 28 hr. (solution took place in about ½ hr.). At that time a sample of the reaction product showed a uv λmax 267 and 297 nm (H₂O, pH 5.5).

The resulting solution was concentrated in a hot water bath at 10 mm pressure to a syrup and further evaporated in an oil bath at 0.1 mm and 100° to yield a viscous liquid to which n-hexane (450 ml) was added. The mixture was refluxed for 1 hr., and the hot, yellowish hexane supernatant was separated from the liquid at the bottom of the round bottom flask.

The resulting light brown oil from which any residual hexane was evaporated in vacuo and dissolved in chloroform (150 ml). This chloroform solution was extracted 8 times with an aqueous saturated solution of NaHCO₃ (250 ml each time). The chloroform layer was then separated, dried (with sodium or magnesium sulfate) and evaporated under high vacuo (0.1 mm) at 40° (water bath) to give a light brown oil which solidified on cooling. This material can be used directly in the next step or purified as follows: The resulting oil was dissolved in 75-100 ml chloroform and n-hexane (ca. 300 ml) added to precipitate out a white crystalline solid which was filtered from the cooled solution. (Extraction is carried out 4-8 times, until carbondioxide is no longer evolved.) This treatment was repeated two more times. Yield: 23.3 g (54%) uv λmax 267, 297 (H₂O, pH 5.5) mp 113°-116°.

ERYTHRO-9-(2-HYDROXY-3-NONYL)6-CHLOROPURINE (VII)

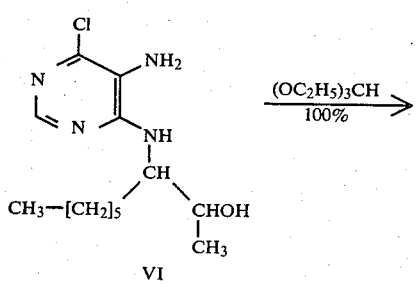

The crude syrup from the preceding operation consisting of erythro-5-amino-4-chloro-6-(2-hydroxy-3-nonylamino)pyrimidine (11.48 g, 40 mmol.) was dissolved in triethylorthoformate (106 ml) and chloroform (34 ml), ethanesulfonic acid (10 drops) was added to effect solution. After standing overnight at 25°, the solution was evaporated to a syrup under vacuo. Yield 11.7 g (quantitative). This syrup consisting of crude erythro-9-(2-hydroxy-3-nonyl)-6-chloropurine (VII) was used in the next step. λMax. 264 nm.

ERYTHRO-9-(2-HYDROXY-3-NONYL)HYPOXANTHINE (VIII)

(By hydrolysis of the 6-chloropurine derivative)

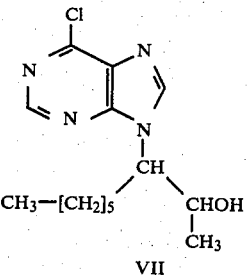

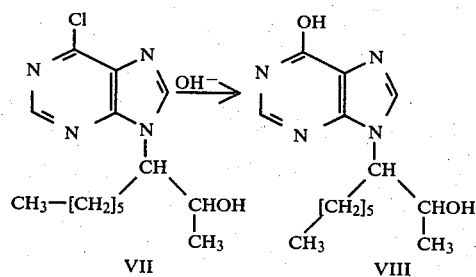

A suspension of erythro-6-chloro-9-(2-hydroxy-3-nonyl)purine (VII, 4.0 g, 13.4 mmol) in 0.5 N NaOH (40 ml) was refluxed for 2 hr. and cooled. Neutralization with glacial acetic acid and cooling gave a crystalline precipitate of erythro-9-(2-hydroxy-3-nonyl)hypoxanthine (VIII) which was filtered and dried. Yield: 3.8 g (quantitative), m.p. 196° uv λmax (pH 5.5) 251 nm.

The crude product (VIII) thus obtained was homogeneous by paper chromatography (3 solvents) and gave negative test for Cl⁻ (copper wire and flame; sodium fusion, acidification and silver nitrate).

Recrystallization of a sample of the crude material 3 times from aqueous ethanol (see Purification) gave colorless crystals. m.p. 202°. Calc. for $C_{14}H_{22}N_4O_2$ (VIII): C, 60.41; H, 7.97, N, 20.13. Found: C, 60.47; H, 7.86; N, 20.08.

PURIFICATION OF ERYTHRO-9-(2-HYDROXY-3-NONYL)HYPOXANTHINE (VIII)

The crude nonyl hypoxanthine (VIII) is purified by recrystallization. The crude material is dissolved by heating in about 6-10 times its weight in ethyl alcohol, and then an equal volume of H₂O is added. The solution is treated with charcoal in an Erlenmeyer and filtered through celite when hot. The solution is evaporated with continuous stirring on a hot plate. Water is added in small portions to replace the evaporated volume until an abundant precipitate appears. Keep on evaporating the solvent to remove all the ethyl alcohol while adding repeatedly H₂O to reach a volume of 8-12 times the weight of material. The loss in material is about 10% per each recrystallization. Two recrystallizations raised the melting point to 202° and gave a colorless crystalline product while the crude material was somewhat yellow or pink and melted at 192°.

ERYTHRO-9-(2-HYDROXY-3-NONYL)-ADENINE. HCl (IX)

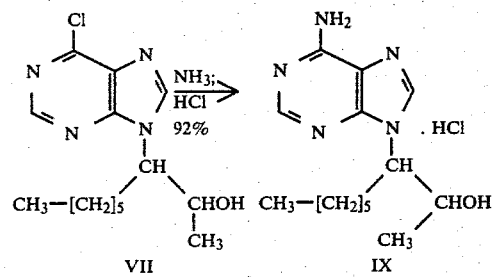

The crude oily erythro-9-(2-hydroxy-3-nonyl)-6-chloropurine (VII) (6.15 g) from the preceding preparations is dissolved in saturated methanolic ammonia (300 ml) and ammonium chloride (1 g) at 80°-100° for 1 hr. in a stainless steel bomb (Parr Instruments). After cooling, the solution was evaporated to dryness in vacuo. Methanol was added and evaporated again (3 times) to eliminate the excess of ammonia.

The syrupy residue was dissolved in absolute methyl alcohol, and dry HCl gas was bubbled, keeping the temperature below 20° (with an ice water bath). After passing HCl for ½ hr., the mixture was cooled at 5°. The precipitate was collected through a sintered glass funnel, washed with cold methyl alcohol and dried in air. Yield 6.0 g (92%); m.p. 173°-175° dec.; uv λmax 260 nm (in H₂O, pH 5.5).

ALTERNATE ROUTE FOR THE PREPARATION OF ERYTHRO-9-(2-HYDROXY-3-NONYL)HYPOXANTHINE (VIII)

(By deamination of VII)

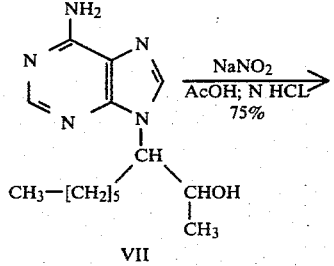

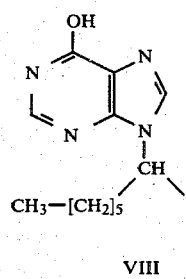

Sodium nitrite (5.6 g, 71 mmole) was added slowly to a solution of erythro-9-(2-hydroxy-3-nonyl) adenine (IX, 4.0 g, 14 mmole) in 50% acetic acid (20 ml) and N HCl (3.2 ml) at 25° with stirring. The mixture was stirred for 2 hr. at 25°. After this time, UV spectrum is monitored. When UV λmax reached 250 mm, the solution was neutralized with 2 N NaOH. The resulting precipitate was filtered and washed with H₂O. Yield=3.03 g (75%); m.p.=195°.

An analytical sample was recrystallized (3x) from water yielding a product m.p. 202°. Anal. Calc. for $C_{14}H_{22}N_4O_2$: C, 60.40; H, 7.96; N, 20.13. Found: C, 60.40; H, 7.90; N, 20.12.

Method K

COMPOUND NPT 15426

There was used the procedure of H. J. Schaeffer and S. F. Schwender, J. Med. Chem. 17:6 (1974).

Method L

PREPARATION OF NPT 15410

0.1 mmoles of 9-(2-hydroxy-3-nonyl)-6-hydroxy purine, NPT 15392 (27.9 mg) and 0.3 mmoles of 2-hydroxy-propyl, dimethylammonium 4-(acetylamino)-benzoate (DIP.PAcBA) (77.1 mg) were accurately weighed and dissolved in 105 ml of 0.25% sodium carbonate ($Na_2CO_3$) to yield a 0.1% solution of NPT 15410 (the compound formed from NPT 15392 and (DIP.-PAcBA) in a 1:3 molar ratio).

EVIDENCE FOR COMPLEX FORMATION

Phase solubility studies carried out with NPT 15392 and DIP.PAcBA demonstrate that NPT 15392 has increased solubility at increasing concentrations of DIP.-PAcBA under conditions of constant pH. This is indicative of an interaction occuring in solution to yield a complex.

In place of the mole ratio of 1:3 (NPT 15392 and DIP.PAcBA), other complexes are formed by using mole ratios of 1:1 and 1:10.

POTENTIATION BY DIP.PAcBA OF BIOLOGICAL ACTIVITIES

Of the substances described in Table 1, NPT 15392 and NPT 15446 are new. Also new are the DIP.PAcBA salts presented in this table, namely, 15428, 15437, 15447, 15432, 15434, 15444, 15418 and 15410. NPT 15392, NPT 15417, NPT 15426 have all been shown to have significant anti-influenza activity by themselves. In one instance (with NPT 15392) the addition of DIP.-PAcBA salt to NPT 15392 to form 15410 does not potentiate the anti-influenza acticity. In the case of NPT 15417, addition of DIP.PAcBA salt to form 15418 does potentiate the anti-influenza activity. A summary of the relative ability of DIP.PAcBA salts to potentiate the different biological activies is set forth below.

| Compound | DIP . PAcBA Salt | Potentiation | | |
|---|---|---|---|---|
| | | Anti-Influenza | Anti-Leukemia | Immunopotentiation |
| 15392 | 15410 | Both equally active | Yes | Yes |
| 15417 | 15418 | Yes | —Yes | |
| 15435 | 15437 | Yes | — | — |
| 15446 | 15447 | Yes | — | |
| 15431 | 15432 | Yes | — | — |

| Compound | DIP . PAcBA Salt | Potentiation | | |
|---|---|---|---|---|
| | | Anti-Influenza | Anti-Leukemia | Immunopotentiation |
| 15433 | 15434 | Yes | — | — |
| 15443 | 15444 | Yes | — | — |

IN VIVO TREATMENT OF MICE WITH NPT 15392 AND NPT 15410: EFFECT ON THE IN VITRO STIMULATION OF SPLEEN CELL PROLIFERATION BY CONCANAVALIN A

The purpose of this study was to determine the effects of in vivo treatment of mice with the compounds NPT 15392 and 15410 on the subsequent activity of spleen cells isolated from these animals and evaluated in vitro for their proliferative response to the mitogen, Concanavalin A (Con A).

PROCEDURE

In Vivo Treatment

Nine male Balb/c mice, 8–9 weeks old, weighing 18–20 gms were divided into three groups. One group was treated twice daily (for 1 day), in the morning and afternoon, with an oral dose of NPT 15392 at 10 mg/kg. The second group was similarly treated with NPT 15410 at 20 mg/kg. A third group, dosed with saline served as a placebo control.

In Vitro Spleen Cell Assay

Cell Preparation

The following day, each group was sacrificed and the spleens removed and pooled. The spleens were minced and the cells washed in RPMI-1640 medium (Grand Island Biologicals) supplemental with 2 mM glutamine and antibiotics. The cell concentration of each preparation was determined by a Coulter counter and adjusted to $5 \times 10^6$ cells/ml with RPMI medium.

Microtiter Plate Assay

Microtiter assays were carried out in 0.2 ml incubations, containing $5 \times 10^5$ cells and Con A or Con A and compounds at the indicated concentrations. All assays were performed with 6 replicates and compared with a blank assay containing only cells. The assay plates were incubated at 37° in 5% $CO_2$ for 4 days. During the final 18–20 hours of incubation, 0.5 ml of $^3$HTdR (10 μCi/ml, 6 Ci/m mole) were added to each culture. The cultures were harvested with a multiple automatic sample harvester (MASH) unit and the incorporated $^3$HTdR determined with a Beckman LS 8000 liquid scintillation counter, as a measure of cell proliferation. The results are tabulated as the ratio of the activity in the Con A or Con A and compound treated cultures to the blank cultures.

In vivo treatment with either compound 15392 or 15410 increases the subsequent response of the spleen cells, in vitro, to Con A stimulation at a suboptimal mitogen concentration (5 μg/ml. A stimulation ratio of 120:1 was observed in spleen cells isolated from mice treated with 15392 as compared to a ratio of 40:1 in spleen cells isolated from mice treated with placebo. No significant differences are obtained with either compound 15392 or 15410 treatment when the cells are stimulated with a more optimal concentration of Con A (10 μg/ml).

There was also tested the effect of subsequent in vitro treatment of Con A stimulated cells with NPT 15392 and 15410 at 1 μg/ml. Both compounds show a marked ability to augment the Con A stimulation, particularly at the suboptimal mitogen concentration (5 μg/ml) and to a lesser extent at 10 μg/ml. At 5 μg/l of Con A, the stimulation by NPT 15392 is 2.8 fold over Con A alone, while that for NPT 15410 is 3.3 fold.

These results indicate an immunomodulating effect of these compounds on spleen cell proliferation. Pre-treatment of animals with either compounds will sensitize the cells to subsequent mitogenic stimulation while exposure of the cells in vitro to the compounds following mitogenic stimulation will augment the proliferative response.

What is claimed is:

1. A compound of the formula

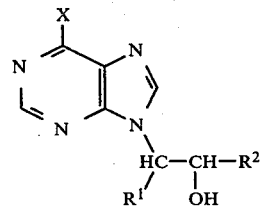

where X is OH, $R^2$ is $CH_3$ and $R^1$ is alkyl of 1 to 8 carbon atoms.

2. A compound according to claim 1 where $R^1$ is normal alkyl.

3. A compound according to claim 2 where $R^1$ is normal alkyl of 1 to 7 carbon atoms.

4. A compound according to claim 3 where $R^1$ is normal alkyl of 1 to 6 carbon atoms.

5. A compound according to claim 4 where $R^1$ is n-hexyl.

6. A compound according to claim 4 where $R^1$ is methyl.

* * * * *